United States Patent [19]

Heinzelman et al.

[11] 4,447,482
[45] May 8, 1984

[54] WOUND CLOSURE TAPE AND APPLICATOR THEREFOR

[75] Inventors: Bert D. Heinzelman, North Bergen, N.J.; Douglas M. Spranger; Malcolm J. Brookes, both of New York, N.Y.; John E. Kuphal, West Linn, Oreg.

[73] Assignee: Shur Medical Corporation, Beaverton, Oreg.

[21] Appl. No.: 452,749

[22] Filed: Dec. 29, 1982

Related U.S. Application Data

[63] Continuation-in-part of Ser. No. 341,487, Jan. 21, 1982, abandoned.

[51] Int. Cl.³ .................... A61F 13/00; B32B 35/00
[52] U.S. Cl. ........................... 428/42; 156/540; 156/577; 156/579; 156/584; 225/2; 225/106; 428/352
[58] Field of Search ............ 156/523, 527, 540, 541, 156/574, 577, 579, 584; 225/2, 4, 106; 428/42, 352

[56] References Cited

U.S. PATENT DOCUMENTS

| | | | |
|---|---|---|---|
| 2,095,894 | 10/1937 | Tarr | 156/527 |
| 2,493,737 | 1/1950 | Burns | 156/523 |
| 2,560,241 | 7/1951 | Pangburn et al. | 156/577 |
| 2,569,140 | 9/1951 | Avery | 156/536 |
| 2,845,041 | 7/1958 | Karn | 118/257 |
| 3,222,242 | 12/1965 | Ingalls et al. | 156/584 |
| 3,274,038 | 9/1966 | Karn | 156/247 |
| 3,283,886 | 11/1966 | Addis et al. | 156/540 |
| 3,308,002 | 3/1967 | Hurwich et al. | 156/577 |
| 3,369,951 | 2/1968 | Fritzinger | 156/523 |
| 3,468,743 | 9/1969 | Soriano | 156/584 |
| 3,586,587 | 6/1971 | Boyce | 156/527 |
| 3,706,626 | 12/1972 | Smith et al. | 428/42 |
| 3,837,952 | 9/1974 | Mogford | 156/540 |
| 3,861,988 | 1/1975 | Preisler | 156/577 |
| 4,060,444 | 11/1977 | Schweig, Jr. et al. | 156/391 |
| 4,151,039 | 4/1979 | Lash | 156/584 |
| 4,188,251 | 2/1980 | Grass et al. | 428/42 |
| 4,240,867 | 12/1980 | Diegel | 156/543 |
| 4,267,949 | 5/1981 | Hemgren | 225/106 |
| 4,302,500 | 11/1981 | Flora | 428/284 |
| 4,330,357 | 5/1982 | Collins | 156/584 |
| 4,336,097 | 6/1982 | Van Kampen et al. | 156/527 |

Primary Examiner—Michael G. Wityshyn
Attorney, Agent, or Firm—Klarquist, Sparkman, Campbell, Leigh & Whinston

[57] ABSTRACT

A wound closure tape applicator has an elongated trapeziform casing partitioned into a front supply chamber for a roll of adhesive tape carried on a backing strip or liner and a trapeziform rear storage chamber for collecting waste backing strip. Front and bottom walls of the casing form a tape outlet slot in a lower front corner of the supply chamber. A cylindrical post extending horizontally between the casing sidewalls internally adjacent the slot guides the tape downwardly along the front wall. A front end portion of the bottom wall projects upwardly close to the underside of the post and guides the liner rearwardly to peel it away from the tape as the latter is pulled downwardly through the opening. A false bottom wall in the casing guides the liner rearwardly along the bottom wall beneath the partition into the rear chamber. The front wall includes a brake flap which is resiliently deflectable to press the tape against the post to separate an applied segment of the tape from the roll along the perforations and to control tension in the tape being applied. The tape but not the liner is perforated and notched at regular intervals along its length. The tape is preset or "aged" in roll form so that when the waste liner is fed into the storage chamber it will coil without regard to the shape of the chamber.

9 Claims, 6 Drawing Figures

U.S. Patent May 8, 1984 4,447,482
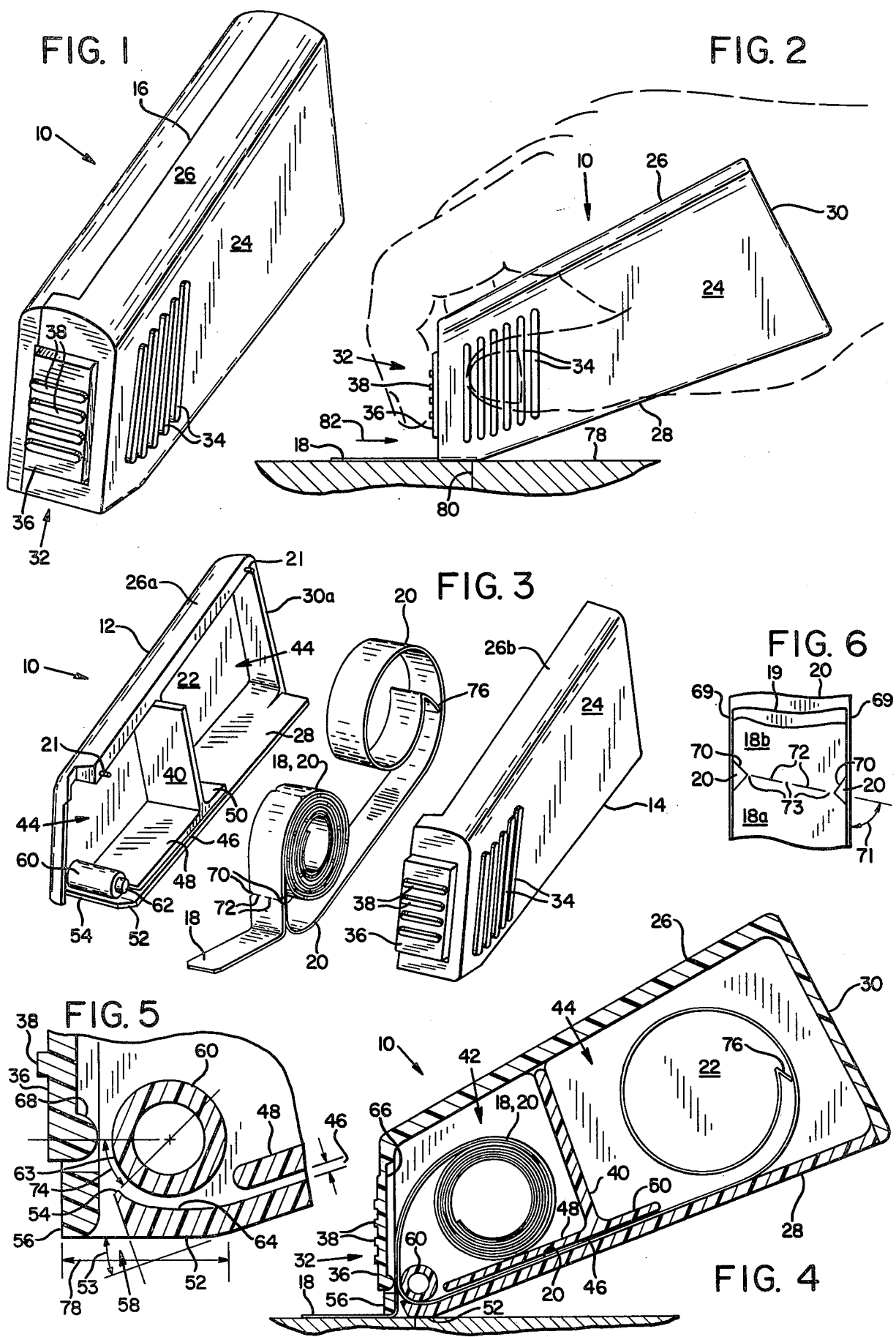

WOUND CLOSURE TAPE AND APPLICATOR THEREFOR

This is a continuation-in-part of application Ser. No. 341,487, filed Jan. 21, 1982, for Applicator For Wound Closure Tape now abandoned.

BACKGROUND OF THE INVENTION

This invention relates generally to liner-backed adhesive tapes and to self-feeding, manually operated tape dispensers for separating the adhesive tape from the liner and applying the tape to a surface, and more particularly to a sterile wound closure tape and an applicator for dispensing and applying the tape directly to a lacerated skin surface.

Wound closure tape is typically a flexible, porous plastic or fabric tape with a pressure-sensitive adhesive coating on its underside. Such tape is conventionally provided in short segments adhered to a backing sheet or liner and packaged in a sterile peel-open envelope. The liner is composed of material which resists adherence of the adhesive coating so that the tape segments can be easily peeled away to expose the coating. In operation, each segment of tape must be manually removed individually from the liner. During removal, the segment can coil and often inadvertently adheres to itself or the user. Applying the segment requires that the skin adjacent a wound edge be pulled together with one hand and the tape applied with the other hand. This process is ungainly and time-consuming. Handling the tape also degrades its ability to adhere to the skin and risks contamination of the wound. Accordingly, it would be preferable to dispense and apply wound closure tape to a skin surface without the foregoing disadvantages.

Unbacked adhesive tape rolled on a tubular spindle is well known. However, this form of tape is unsatisfactory for use as wound closure tape. The adherence between the layers of the rolled tape makes stripping tape from the roll difficult. Such tape cannot readily be applied directly from a roll to yieldable surfaces, such as human skin, which are not firm or rigid enough to exert sufficient pulling force to strip the tape from the roll or to easily tear off a length of applied tape. In addition, such tape cannot readily be maintained in a sterile condition until applied, making it unsuitable for use as a wound closure tape.

It has been suggested that liner-backed adhesive tape for medical purposes be provided as a continuous strip in roll form for use with a hand-held dispenser which separates the liner from the tape as the latter is dispensed. Such a suggestion together with dispensers for such tape are found in the identical disclosures of U.S. Pat. Nos. 4,330,357 to Collins and 4,336,097 to VanKampen. However, when using a roll of continuous tape with such a dispenser, a tape cutting means must be provided either on the dispenser itself or separately from it to sever a strip of dispensed tape from the roll. If a separate cutting means, such as scissors, is used to cut a strip from the roll, both hands are occupied in applying the tape, one to hold the dispenser and the other to hold the cutting means, leaving no hand free for performing other necessary procedures. However, if the dispenser is equipped with a built-in cutting means, such as a cutting blade, the cost of manufacturing the dispenser is increased, possibly to an extent such that it would no longer be economical to dispose of the dispenser after it has dispensed a single roll of tape. Furthermore, dispensers with cutting blades present safety hazards unless such blades are well shielded. Such blades also tend to collect adhesive so that they may become ineffective after repeated usage. Adhesive-coated blades can also become contaminated with bacteria, thereby providing a potential source of contamination for the tape before it can be applied to a wound. Accordingly, there is a need for a liner-backed wound closure tape which can be provided in roll form and yet applied in short segments to close a wound without the use of a cutting means. There is also a need for a hand-held applicator which can store a roll of such tape and apply it in short segments directly to a wound without the need for a cutting means, either on the applicator or separately from it, and which can be disposed of when the roll is used up.

The aforementioned Collins and VanKampen patents also disclose a tape dispenser which separates the tape from the liner and propels the waste liner into a liner storage chamber of the dispenser as the tape is pulled from its roll. This is a desirable feature of any applicator for wound closure tape. However, such a dispenser requires that the storage chamber walls be curved to cause the waste liner to coil in the chamber to ensure that the liner will not jam the dispenser. The need for a curved liner storage chamber tends to dictate the overall shape of the dispenser, which for optimum comfort and handling might best be of some other shape. Accordingly, there is also a need for a wound closure tape and applicator therefor which operate such that as the tape is dispensed from the roll and applied to a wound, the waste liner will be stored in coiled form within a storage chamber of the applicator, without regard to the shape of such chamber.

In applying tape from a roll within an applicator across a skin laceration, it is advantageous to place the tape under controlled tension to help close the laceration. In the dispensers of the aforementioned Collins and VanKampem patents, this tension is applied manually by extending a thumb or finger through an opening in the dispenser housing to press an exposed section of the lined tape against an interior wall of the dispenser. The opening and use of direct thumb or finger pressure to apply tension exposes the interior of the dispenser and thus the tape supply roll to contamination from external sources, rendering this approach undesirable for medical purposes. Accordingly, there is a need for an applicator for dispensing wound closure tape from a supply roll of lined tape under a controlled tension without exposing undispensed portions of the tape within the applicator to contamination.

Another problem in dispensing liner-backed adhesive tape from a supply roll within a dispenser is the tendency of the adhesive to be squeezed from between the tape and liner along their edges, gumming up any internal moving parts of the dispenser such as supply and takeup reels. The dispensers of the Collins and VanKampen patents partially avoid the problem by eliminating all internal moving parts. However, the narrow internal tape and liner passageways of such dispensers are subject to partial blockage by free adhesive, which could cause the dispensers to malfunction. Accordingly, there is a need for a liner-backed adhesive wound closure tape and an applicator capable of dispensing such tape from a supply roll without fouling the applicator. There is also a need for an applicator that will deliver adhesive tape from a supply roll of liner-backed such tape smoothly while separating and storing the waste liner in the applicator under all conditions without malfunction. Although various tape dispensers have been proposed in addition to those of the aforementioned Collins and VanKampen patents, none fulfill all of the foregoing needs. Some of such applicators are discussed below.

Numerous devices have been proposed for dispensing or applying unbacked, rolled tape. Examples of self-feeding applicators for such tape are disclosed in U.S. Pat. Nos. 2,493,737 to Burns; 2,560,241 to Pangborn, et al.; and 4,060,444 to Schweig, Jr., et al. However, such devices are not usable to dispense or apply adhesive tape carried on a backing strip or sheet because they lack means for removing such a sheet or a strip. Accordingly, numerous applicators and dispensers of different kinds have been proposed for use with adhesive or pressure sensitive tape carried on a backing strip.

One of the simplest applicators of this type is disclosed in U.S. Pat. No. 3,861,988 to Preisler. This applicator houses a roll of pressure sensitive adhesive sheeting carried on a backing sheet in a cylindrical tube. The sheeting is dispensed through a lengthwise slot in the tube. A compressible pressure bar protrudes outwardly from the external face of the tube at the edge of the slot. By exposing and applying an end of the pressure sensitive sheet to a vertical surface, such as a wall, and pulling the applicator tube downwardly along the surface, the sheeting is rolled onto the surface. The backing sheet automatically peels downwardly away from the pressure sensitive sheeting as the sheeting is pulled upwardly around the pressure bar. However, this applicator is poorly suited for use in applying wound closure adhesive tape to skin surfaces. Preisler discloses no means for taking up the waste backing sheet. Such sheet contacts the wall surface as it peels from the adhesive sheet. Using such an applicator on a horizontal skin surface would drag the waste backing sheet along the skin surface, interfering with application of the tape and risking contamination of the wound.

U.S. Pat. No. 2,569,140 to Avery discloses an applicator which uses a pair of rollers to draw the backing strip rearwardly around a 180° turn to separate it from the tape and to pull it away from the area where the tape is being applied. The lower roller tracks along the surface to which the tape is being applied. It is turned by frictional engagement with the surface, necessitating that the applicator press against the surface with enough force to turn the rollers. Application of such force to a lacerated skin surface is undesirable. This device also provides no means for collecting the waste backing strip. It additionally requires moving parts including rollers, making it expensive to construct and to clean thoroughly. It is, therefore, unsuitable for use in a medical environment, wherein a disposable applicator would be greatly preferred and cleanliness is essential.

U.S. Pat. No. 4,151,039 to Lash discloses a tape dispenser which winds the backing strip on a takeup roller driven by a pulley connected to a spindle supporting the adhesive tape. Lash's dispenser takes up the waste backing strip as tape is dispensed but uses a more complicated mechanism than is preferred. It also lacks means for applying the tape directly to a skin surface.

U.S. Pat. Nos. 2,845,041 and 3,274,038 to Karn disclose devices for applying adhesive coating material rather than tape. In both devices, a layer of adhesive substance is carried on a backing strip which, when pressed against a surface, leaves the adhesive substance behind. Neither of these devices would be useful for applying a selected length of adhesive tape to a skin surface over a wound and then separating the length of tape from the applicator. The earlier Karn patent discloses a chain-driven roller arrangement for pulling the backing strip into a storage chamber. The storage chamber is roughly triangular in shape and the passageway is positioned to feed the waste backing strip into the center of the chamber. This arrangement is undesirable, particularly if the feed rollers are omitted, because the waste backing strip can accumulate in such a way that it blocks the passageway. It is also too complex for economical use as a disposable applicator. The latter Karn patent discloses an applicator designed to wind the backing strip back around the roll to an internal passageway leading upwardly to a tear-off edge or alternatively to a backing strip storage chamber.

U.S. Pat. Nos. 3,468,743 to Soriano and 4,240,867 to Diegel disclose adhesive tape dispensers which employ peel blades to separate the adhesive tape from its backing. These devices are unsatisfactory generally because the adhesive material can stick to the peeling blade. They are unsuitable for medical use because of the potential for contamination of the wound closure tape by the peeling blade. Both devices also lack means for accumulating the backing strip as it is removed from the adhesive tape.

Other label and tape dispensers are disclosed in U.S. Pat. No. 3,222,242 to Ingalls, et al.; No. 3,308,002 to Hurwich, et al. and No. 3,369,951 to Fritzinger. All of these devices are quite complex, requiring numerous moving parts for their operation, and therefore are unsuited for applying wound closure tape.

Accordingly, there remains a need for a simple, sanitary and effective applicator for wound closure tape carried on a liner or backing strip.

SUMMARY OF THE INVENTION

A primary object of the invention is to provide a liner-backed adhesive wound closure tape in roll form from which tape segments can be applied to a wound and separated from the roll without the use of a cutting blade.

Another primary object is to provide a hand-held applicator which can be operated with one hand to apply the aforesaid tape, separate the tape from its liner as the tape is applied, coil the liner in a storage chamber of the applicator, tension the tape during its application, and separate the applied tape segment from its supply roll, all without the need for a cutting means or internal moving parts.

Another primary object is to provide a wound closure tape as aforesaid that will cause the waste liner to coil within a storage chamber of an applicator regardless of the shape of such chamber.

Yet another important object is to provide a wound closure tape as aforesaid that will not foul the applicator with which it is used with adhesive.

Still another important object is to provide an applicator as aforesaid with sanitary means for applying a controlled tension to the tape as it is applied as an aid for drawing the edges of a wound together and for separating the applied tape segment from its supply roll without contaminating the tape.

Other important objects are to provide an applicator which is economical to manufacture, easy to operate with one hand, comfortable to use, and reliable to operate.

Still other important objects are to provide an applicator as aforesaid which has no moving parts and is so economical to make that it is disposable after its tape supply is consumed.

A wound closure tape of the invention and especially suited for use in the applicator of the invention comprises a length of surgical tape having a pressure-sensitive adhesive coating on one side and a liner or backing strip releasably adhered to the coating. The liner-backed tape is wound into a supply roll for insertion into a supply chamber of the applicator. The roll is preferably preset, that is, maintained in roll form for a substantial period of time before being inserted in the applicator so that the liner when stripped from the tape will tend to coil of its own accord. The tape, but not the backing strip, is perforated at intervals along its length before it is wound into a roll for easy separation into segments. Each set of perforations preferably terminates at an opposed pair of notches along the opposite marginal edges of the tape to provide the user with a visual indication of the end of a segment and a focus of force for tearing a tape segment from the roll along the perforations. Each set of perforations may comprise one or more die-cut slits between a pair of notches. The notches and slits are spaced to provide narrow interconnections between the tape segments. The backing strip is sufficiently rigid that it can be pushed through a narrow passageway and into a coil in the storage chamber. The tape is relatively inelastic to minimize stretching during application, and its adherence to the liner is low so as to easily separate therefrom in a peeling action without bending the backing strip. The opposed notches may be longitudinally offset from one another slightly and the slits may extend diagonally between the notches at, for example, about 80°, to the edges of the tape so as to ensure noninterference of the notches with the various guiding surfaces of the applicator. The liner is also preferably slightly wider than the tape so as to extend slightly beyond the opposite side margins of the tape so as to shield the internal structure of the applicator from adhesive on the tape.

An applicator in accordance with the invention comprises a casing sized to fit within the hand of a user. The casing defines a tape supply chamber for storing the liner-backed wound closure tape in roll form. The casing has a tape outlet slot, preferably positioned at the lower front corner of the casing at the intersection of its front and bottom walls to provide optimum visibility of the wound site during application of the tape. The applicator includes means for separating the liner from the tape as it is pulled from the supply chamber through the outlet slot and means for guiding the separated waste liner in a self-feeding action driven by the pulling of the tape through the outlet slot, into a liner storage chamber adjacent the supply chamber.

The separating means may include a cylindrical post at the lower front corner of the applicator inside the casing and just above the outlet slot. The separating means may also include an upwardly and inwardly projecting front end portion of the bottom wall. With such an arrangement, an inside guiding surface of the front wall and opposing guiding surfaces of the post and forward end of the bottom wall define a tape passage which directs the tape downwardly and out of the applicator through the outlet slot. An inside guiding surface of the projecting front end portion of the bottom wall defines with an opposed guiding surface of the post a first liner passage or guideway diverging away from the tape passage or guideway to induce peeling of the liner away from the tape as the tape is pulled through the outlet slot. A second liner passage or guideway forming a continuation of the first liner pasage may be defined by an inside surface of the bottom wall rearwardly of the forward end portion thereof and an interior partition of the casing paralleling the bottom wall. This second liner passage guides the waste liner into its storage chamber where such liner coils itself. The second passage may extend partially into the storage chamber along the bottom wall so that the waste liner does not begin to coil prematurely.

A brake or tensioning means may include a depressible flap portion of the front wall opposite the post. By depressing the flap portion, a section of liner-backed tape just upstream of the separating means is pressed by the flap portion against the post to tension a segment of tape being applied to the skin. Such tension can be applied selectively to either pull two edges of lacerated skin together or separate an applied tape segment from its roll at a perforation.

The casing may be internally partitioned to define the supply and storage chambers. The storage chamber is preferably quadrangular or trapeziform in shape to minimize friction between the waste liner and the walls of the storage chamber while maximizing its effective diameter. The supply chamber is also preferably trapeziform.

The foregoing and other objects, features and advantages of the invention will become more readily apparent from the following detailed description of a preferred embodiment of the invention, which proceeds with reference to the accompanying drawing.

BRIEF DESCRIPTION OF THE DRAWING

FIG. 1 is a perspective view showing the front, top and left sides of a tape applicator in accordance with the invention.

FIG. 2 is a side elevational view of the applicator of FIG. 1 in position in a user's hand, shown in phantom lines, for applying a strip of wound closure tape to a skin surface.

FIG. 3 is an exploded perspective view of the applicator of FIGS. 1 and 2, with the roll of adhesive tape carried on a backing strip positioned between the halves of the casing.

FIG. 4 is a longitudinal cross-sectional view of the tape applicator as shown in FIG. 2.

FIG. 5 is an enlargement of the lower front corner of the casing of FIG. 4, the tape being omitted for clarity.

FIG. 6 is an enlarged top plan view of a length of wound closure tape usable in the applicator of FIGS. 1-5, portions being cut away to show underlayers.

DETAILED DESCRIPTION OF PREFERRED EMBODIMENT

Tape Applicator

Tape applicator 10 comprises an elongated casing made up of right and left casing halves or shells 12, 14 mated together along a longitudinal dividing line 16 and housing a roll of surgical tape 18 adhered by a pressure sensitive coating 19 to a backing strip or liner 20. The casing is symmetrical about line 16 so that it can be used in either hand. The halves of the casing are separately formed of suitable plastic, such as LEXAN 141, and ultrasonically welded together with a roll of adhesive tape 18 on backing 20 inside. Referring to FIG. 3, alignment pins 21 are formed in the upper corners of shell 12 along the dividing line for insertion into complementary holes (not shown) in shell 14.

Referring to FIG. 2, the applicator has a trapeziform external shape and is sized to fit comfortably in the user's hand. It has a pair of parallel, flat sidewalls 22, 24. A transversely rounded top wall 26, a flat bottom wall 28, a flat rear wall 30 and generally flat front wall 32 extend between the sidewalls. Rearwardly adjacent the front wall, on the outer surface of each sidewall, a series of spaced apart gripper ribs 34 extend parallel to the front wall to aid in grasping the applicator between the user's thumb and fingers. The front wall includes an integral resiliently deflectable flap brake 36 hinged along its upper edge and provided with an array of vertically spaced apart horizontal gripper ribs 38.

Referring to FIGS. 3 and 4, the casing is internally divided by a partition 40 joining top wall 26a and sidewall 22 in the right half of the casing. This partition divides the casing lengthwise into a front tape supply chamber 42 for housing the unused roll of tape 18, 20 and a rear storage chamber 44 for receiving the backing strip after it is peeled from the tape. Both chambers are trapeziform in shape and chamber 44 is somewhat larger than chamber 42. The interior corners between partition 40, top wall 26, back wall 30 and bottom wall 28 are filleted to provide smoothly curved transitions from one wall to the next.

The lower end of partition 40 terminates in flanges 48, 50 paralleling and spaced above bottom wall 28 to provide with the bottom wall a passage or guideway 46 for the backing strip. Flange 48 extends forwardly from partition 40 and forms a false bottom wall or partition in the front chamber 42. It is spaced above and parallel to bottom wall 28 to form a guideway for guiding the waste backing strip rearwardly along the bottom wall and through passageway 46 to the rear chamber. Similarly, flange 50 extends rearwardly from the lower end of partition 40 a short distance into chamber 44 to hold the backing strip against the bottom wall 28 well into the rear chamber.

The bottom wall 28 has a flat upturned front end portion 52 which is inclined upwardly in a forward direction at an angle 53, for example, 20°, from the remainder of the bottom wall. Portion 52 has an upwardly projecting, tapered, blunt front end 54 spaced from a fixed lower end 56 of the front wall to define at the intersection of the two walls a tape outlet slot 58, best seen in FIGS. 4 and 5. End 54 is tapered inwardly and squared off to form a lip at which the tape and liner passages begin to diverge. This lip and the front surface of the bottom wall below it are spaced rearwardly of the front wall a sufficient distance to avoid contact with the adhesive tape so as to avoid contaminating the tape or sticking to its adhesive undercoating.

The lower end 56 of the front wall is rounded along slot 58 to provide a smooth convex path for the tape to be pulled around in a forward direction from the applicator. The lower terminus of end 56 is horizontally aligned with the outer surface of bottom end portion 52 for pressing the tape against a skin surface as it is dispensed.

Spaced just above bottom wall portion 52 and just rearwardly of front wall 32 at the inside corner between the two walls is a cylindrical post 60 extending horizontally between the sidewalls. The post is integrally formed in the right casing shell 12 and has a smaller diameter end portion or alignment pin 62 which is inserted into a complementary hole (not shown) in the left casing shell 14 during assembly. The front face of the post forms a convex first guiding surface 63 spaced closely adjacent front wall 32 to define a tape passage for guiding the tape and backing strip downwardly along the front wall toward slot 58.

The bottom wall portion 52 has an upwardly projecting, slightly concave inside surface 64 providing a second guiding surface approximately concentric with opposing surface 63 of the post and spaced below the post to define a first liner passage or guideway. The aforementioned flanges 48 and 50 of partition 40 define with the inside surface of the bottom wall of the casing the second liner passage 46 which is a rearward continuation of the first liner passage. Surface 64 and its defined liner passage diverge rearwardly from the downward tape path or passage through slot 58 to cause the backing strip to peel away from the tape as the tape is pulled through slot 58 and forwardly around the lower end 56 of the front wall means. It is the divergence of the tape and liner passages at lip 54 which causes separation of the liner from the tape. Lip 54 does not act as a peeling knife and adhesive does not build up at this point. The radii of surfaces 63, 64 are determined by the angle between the downward path of the tape and guideway 46. Greater radii would be used if this angle is more acute than shown in FIG. 5.

The brake flap 36 is integrally formed as part of the front wall. A thin wall section 66 at the connection of the flap and wall provides a hinge so that the flap's lower end can be depressed against post 60. When released, the flap springs away from the post to its normal position shown. The lower end of the flap has an enlarged, generally rounded lobe or bar 68 extending horizontally along its inner side adjacent the post. This lobe could be pointed if desired. The lower end of the flap is normally spaced a sufficient distance from the post to provide free movement of the tape and backing strip therebetween. When manually depressed, the flap moves in a pivotal fashion about its hinge 66 to press the tape and backing strip against the guiding post surface 63 and thereby tension or brake the tape in the applicator. An alternative form of braking means might include a frustoconical post (not shown) formed in a sidewall of the supply chamber in position to project inside and engage a tubular spool (not shown) carrying tape roll 18, 20 when the sidewalls are squeezed together, thereby braking the spool to tension the tape.

Wound Closure Tape

The tape 18, coating 19 and backing strip 20 are designed to cooperate with various features of the applicator to self-feed the tape from the casing and the waste backing strip into the rear chamber and to enable easy separation of selected sections of tape applied to a skin surface. A suitable liner-backed adhesive tape composition for this purpose is the SHUR-STRIP random fiber surgical adhesive tape, manufactured by Shur Medical Corporation of Beaverton, Oregon, under U.S. Pat. No. 4,302,500, incorporated by reference herein.

Referring to FIG. 6, the backing strip is preferably about 0.04 inches wider than the tape and the tape is centered on the strip. This arrangement provides 0.02 inch backing strip margins 69 along the margins of the tape to space the adhesive coated edges of the tape from the sidewalls of the casing and thereby avoid inadvertent adherence thereto.

The tape has opposed right angle V-shaped notches 70 formed at lengthwise intervals along both margins to divide the tape into segments 18a, 18b. These notches provide visual indicators to the user of where one tape segment ends and another begins to signal when an applied segment should be separated from its roll. The notches also provide a focus for tearing forces when the brake flap is applied to facilitate separation of a segment from the roll. Extending between the vertices of each pair of opposed notches are perforations comprising two die cut slits 72. The opposed notches are offset along the length of the tape so that the slits form a non-right angle 71 of less than about 85°, preferably 80°, with the edges of the tape. The slits and notches are spaced 0.020 inches apart to provide readily visible interconnections 73 between the tape segments in the aforementioned random fiber tape which are readily breakable when the tape is separated from the backing strip but not otherwise. If desired, however, the notches and perforations may extend normal to the marginal edges of the tape.

The notches and slits are formed only in the tape; the backing strip is not notched or perforated so as to provide uniform rigidity along its length. This feature ensures that the waste backing strip is sufficiently rigid that it will peel away from the tape and be pushed along bottom wall surface 64 and rearwardly through passageway 46 into the storage chamber. The adherence of the coating to the backing strip must be low enough and the backing strip rigid enough for the tape to be easily peeled from the strip without bending the strip so that it buckles or is drawn into the outlet slot. A silicone backing strip material of about 63 lb./ream provides the desired rigidity and adherence characteristics. The rigidty of the backing strip also enables the waste backing strip to be pushed through guideway 46 to form a coil in the rear chamber 44. The rear flange 50 extends rearwardly into the storage chamber a sufficient distance to prevent waste backing strip from arching upwardly from bottom wall 28 to accumulate in accordion-like loops (not shown) weaving back and forth in the chamber. A greater length of backing strip can thus be accumulated in the rear chamber without jamming than would otherwise be possible.

It is the nature of the roll of tape itself that causes the waste liner or backing strip to coil in the storage chamber. The liner material described has a memory so that when the liner-backed tape is wound into a tight roll and "preset", that is, maintained in such roll form for an appreciable length of time, usually a minimum of about 2 hours at room temperature, the waste liner will coil of its own accord if unconstrained. Thus, when the waste liner enters the storage chamber, it coils without regard to the shape of the chamber walls. Thus, the applicator can be designed for optimum appearance and functionality without the need to consider any peculiar shape requirements of the storage chamber. It has been found that a liner or backing strip of 3 to 7 mils thickness and composed of a semi-bleached paper which is release-coated with silicone on both sides has the desirable memory characteristics described.

In loading the applicator with a supply roll of the tape, a short leader of waste liner is threaded around the lower side of post 60 along guide surface 64 and a short distance into guideway 46, but without extending the leader all the way into storage chamber 44. It has been found that by preparing the applicator in this manner, the curvature of post 60 and guide surface 64 will help maintain the set of the leader to ensure that it will coil when it later enters the storage chamber as tape is pulled through the outlet slot 58.

EXAMPLE

In one example, an applicator for ½ inch wide wound closure tape has an overall length of approximately 3.7 inches. Partition 40 is positioned 1.125 inches to the rear of the axis of post 60. The rear chamber 44 thus has an internal length one and a half to two times that of the front chamber 42. The external vertical dimension of the rear wall 30 is approximately 1.75 inches. The corresponding dimension of the front wall means is approximately 1.225 inches, of which flap 36 constitutes about 1.003 inches. The flap's upper end 66 is 0.030 inches thick. The distance along end portion 52 of bottom wall 28 to the lower front corner of the front wall means, as indicated by arrow 78, is 0.446 inches. Post 60 has a radius of 0.125 inches. The axis of the post is 0.218 inches above the lower surface of bottom wall portion 52 and 0.157 inches rearwardly of the inner surface of the front wall means, vertically adjacent the enlarged lobe end 68 of flap 36. The upper face 64 of bottom wall portion 52 is spaced 0.152 inches below the axis of the post. The blunt end 54 of such portion is a maximum of 0.015 inches wide and is positioned along a line through the post axis at an angle 74 at least 50° from horizontal. The spacing between flanges 48, 50 and the bottom wall is 0.027 inches and the horizontal width (not shown) of passageway 46 is 0.60 inches. Flange 50 extends 0.5 inches rearwardly from the centerline of partition 40.

The casing halves 12, 14 can be constructed as shown in the drawing by conventional machining techniques. To make such a casing by injection molding techniques, it is preferable to form flanges 48, 50 on the casing half 14 opposite that in which bottom wall 28 is formed to obtain better control of spacing tolerances. A complementary keyway or channel is molded in the interior of the sidewall of the casing half 12 to more positively control the spacing of such flanges above the bottom wall during assembly. Post 60 is preferably molded separately as a cylindrical tube, as shown in FIGS. 4 and 5. Locating bosses (not shown) are molded into the casing halves to fit inside the cylinder to position it in the casing as described above. Molding draft angles also need to be coordinated to maintain substantially parallel (±0.5°) relationship from side to side between guiding surfaces 63 and 64, between surface 63 and brake lobe 68, and between bottom wall 28 and flanges 48, 50.

OPERATION

The wound closure tape applicator is provided fully assembled in a sterile, peel-open package (not shown) suitable for surgical use. A preset roll of tape 18 on its backing strip 20 is loaded in the front supply chamber 42, and a short leader of the backing strip is threaded about post 60 and into guideway 46 as previously described. The free end of the backing strip may be folded back at an acute angle if desired to form a leader end 76 although this is not necessary with the use of the previously described tape. As backing strip is added to the rear chamber, leader end 76 tends to hold the free end of the strip away from the walls so that it does not catch in corners. The leader also tends to hold such end away from the sidewalls and later-added coils to minimize friction therebetween.

A free end (not shown) of the tape extends through slot 58 and can be adhered either to bottom wall portion 52 or to a short length of backing strip (not shown). To use the applicator, this free end is detached from the casing or backing strip. Additional tape is then pulled out through the outlet slot to expose the first pair of notches 70, torn off and discarded. Referring to FIG. 2, the next segment of tape is then applied to skin surface 78 on one side of wound 80. The applicator is then pulled rearwardly along the skin surface, as indicated by arrow 82, until the next set of notches is visible. The adherence of the tape to the skin pulls additional tape under minimal tension from the front chamber 42 as the lower end 56 of the front wall presses it against the skin surface. This action feeds the backing strip downwardly around post 60 and rearwardly along bottom wall portion 52 through guideway 46 and into the rear chamber 44, thereby peeling it from the tape and coiling it in the storage chamber in a self-feeding action. When a segment of tape has been applied to the skin surface, flap 36 is depressed by the user's index finger to actuate the brake flap. Tugging gently on the casing separates it from the applied tape segment at the pair of the notches 70 adjacent to the casing. The flap is then released and the process of applying tape segments can be repeated. The flap can also be used to increase tension on a tape segment being applied to the skin to help pull opposed edges of the skin together to close a laceration. When all the tape has been used, the applicator is discarded.

Having illustrated a preferred embodiment of the invention, along with a specific example thereof, it should be apparent that modification in arrangement and detail can be made without departing from the principles of the invention. We claim all such modifications as come within the spirit and scope of the following claims.

We claim:

1. A sterile wound closure adhesive tape product for use with a tape applicator, said tape product comprising:
   a single strip of surgical tape having a pressure sensitive adhesive coating on one surface and a releasable backing strip covering the adhesive-coated surface,
   said strip of tape being transversely perforated at regular intervals along its length to subdivide the strip into joined tape segments separable along the perforations without the aid of a cutting device upon the application of a substantial tensile force at said perforations, the length of each segment being substantially greater than its width,
   said releasable backing strip being continuous and imperforate throughout its length,
   said tape and backing strip being wound together into a supply roll for installation in an applicator,
   said strip of tape but not said backing strip including a pair of opposed notches one at each of the opposite marginal edges of said tape aligned with the perforations dividing said tape segments to provide a visual indicator of an end of each segment and an aid to separation of segments from the supply roll upon application of said tensile force,
   said strip of tape being slightly narrower than said backing strip and being positioned on said backing strip such that both marginal edge portions of said backing strip extend slightly laterally outwardly beyond the corresponding marginal edge portions of said tape strip,
   said supply roll being preset to cause said backing strip to self-coil when unconstrained after its release from said strip of tape,
   said perforations being arranged to provide sufficient tensile strength at the interconnections between tape segments such that application of a segment to a skin surface under sufficient tension from the supply roll to close a laceration of such surface does not separate the applied segment from the roll.

2. A product according to claim 1 wherein each set of notches and perforations extend diagonally across said tape to form an acute angle with the marginal edges of said tape.

3. A product according to claim 1 wherein said tape strip is composed of a porous random fiber material and said adhesive and said backing strip is composed of a strip of paper release coated with a silicone release material on both surfaces, said backing strip having a thickness in the range of 3 to 7 mils,
   each transversely perforated interval along said tape comprising at least one slit extending through the tape and across a portion of the width thereof in alignment with a pair of said notches but spaced from said notches to provide narrow interconnections between said tape segments,
   said interconnections being about 0.02 inches wide.

4. A wound closure adhesive tape product for use with a tape applicator, said tape product comprising:
   a strip of surgical tape having a pressure sensitive adhesive coating on one surface and a releasable backing strip covering the adhesive-coated surface,
   said strip of tape being transversely perforated at regular intervals along its length to subdivide the strip into joined tape segments separable along the perforations upon the application of a tensile force at said perforations,
   said releasable backing strip being continuous and imperforate throughout its length,
   said tape and backing strip being wound together into a supply roll for installation in an applicator,
   said strip of tape includes a pair of opposed notches one at each of the opposite marginal edges of said tape aligned with the perforations dividing said tape sections,
   said opposed notches of a pair being slightly offset from one another along said tape.

5. A disposable applicator for applying a liner-backed sterile surgical adhesive tape from a supply roll of such tape comprising:
   a casing sized to fit within the hand of a user, including wall means defining a tape roll supply chamber, a separate waste liner storage chamber, and passage means interconnecting said chambers,
   said casing including external front and bottom walls defining a tape outlet slot therebetween,
   a guide post at the inside corner between said front and bottom walls and spaced inwardly therefrom and above said slot,
   an external surface of said guide post and spaced inner surface of said front wall defining a guide path for the lined tape from the supply chamber toward said outlet slot,
   an external surface of said guide post and spaced inner surface of said bottom wall defining a guide path for waste liner toward said passage means,
   and said post, front wall and bottom wall surfaces being interrelated so as to define divergent paths for said tape and liner to cause their separation at the divergence of their paths, said front wall including a resilient depressible front wall portion engagable with a surface of said post to press a section of tape passing therebetween against said post, said casing being generally quadrangular in shape as defined by generally flat and straight external walls, said supply and storage chambers being of quadrangular shape and defined in part by said external walls.

6. An applicator according to claim 5 wherein said front wall is straight and said bottom wall is angular and includes a short upturned but flat forward bottom wall portion which approaches a lower front wall portion at substantially a right angle in the region of said outlet opening, the lower terminus of said front wall and the bottom surface of said forward bottom wall portion lying in a common plane for use in applying pressure against the skin during application of the tape to the skin.

7. A blade-less, disposable surgical tape applicator system comprising in combination:

a casing sized to fit within the palm of the hand of a user and partitioned internally to define a tape supply chamber and a waste liner storage chamber, a tape outlet slot at a lower forward corner of said casing leading from said supply chamber and formed by converging wall portions of said casing, a rigid internal guide surface spaced inwardly of said slot within said casing at said corner and defining with said converging wall portions divergent guide paths including a tape path leading from the supply chamber to said outlet slot and a waste liner path leading from the supply chamber toward said storage chamber, internal partition means extending along and spaced from a bottom wall of said casing rearwardly of said guide surface to define with said bottom wall a waste liner passage as a continuation of said liner path, said passage communicating at opposite ends with said supply chamber and said storage chamber, a supply roll of liner-backed sterile surgical adhesive tape loosely positioned within said supply chamber for centerless rotation therein, said tape, but not said liner, being divided at regular intervals along its length into connected segments by transverse perforations terminating at opposed marginal edge notches providing visual indications of the divisions between segments and a focus for tensile separating force applied across said perforations to facilitate separation of each segment from said roll, an unlined leader portion of said tape extending from said roll across said internal guide surface and along said tape path through said outlet slot, a leader portion of said liner extending with said tape across said guide surface and thence diverging from said tape along said liner path and into said liner passage, said outlet slot, guide surface and divergent paths being operable such that as said tape leader is withdrawn through said slot said liner is separated therefrom and propelled along said passage into said storage chamber, said roll being preset in roll form to an extent such that as said liner enters said storage chamber it self-coils independently of the shape of said chamber, the tensile strength of said perforated tape portions being such that sufficient tension can be applied to the tape across a perforated tape portion during application of a tape segment to a skin surface to close a wound without separating the applied segment from the roll, and being such that application of a higher tension to the tape across a perforated tape portion separates the applied segment from the roll without the aid of any cutting means, said casing including a resilient depressible wall portion depressible by selectively applied hand pressure and cooperative with said guide surface to apply a controlled variable tension to the tape including a low tension for closing a wound and thereafter a higher tension for separating an applied segment from the roll without the aid of any cutting means.

8. The combination of claim 7 wherein said outlet slot is provided at a lower front corner of said casing at an intersection of front and bottom walls of the casing, said wall means defining said divergent paths includes a lower inside surface of said front wall, a concavely curved inside surface of said bottom wall, and said internal guide surface comprising a post having a convexly curved surface spaced inwardly from said lower inside front wall surface and said concavely curved inside bottom wall surface at the inside corner between said front and bottom walls, said depressible wall portion including tape braking means comprising a resilient depressible flap portion of said front wall operable upon application of finger pressure thereto to selectively press a section of tape passing along said front wall against a surface portion of said post to enable separation of an applied segment of said tape from said roll.

9. A surgical tape applicator system according to claim 7 wherein said casing is of generally thin, flat, quadrangular shape, as defined by generally flat, parallel opposed external side walls interconnected by generally straight, flat external front, rear, top and bottom walls, a first straight interior partition extending from said top wall toward and generally perpendicular to the bottom wall to subdivide the interior of said casing into a forward tape supply chamber of generally quadrangular shape and a larger rear waste liner storage chamber of generally quadrangular shape, said internal partition means extending along the bottom wall of said casing comprising a second interior partition extending perpendicular to and intersecting said first interior partition, said second partition including a forward portion extending forwardly from said first partition into said supply chamber and having a forward end terminating adjacent to said internal guide surface and a rear portion extending rearwardly from said first partition to a rear end terminating within said storage chamber, said guide surface comprising a stationary post having a convexly curved external surface, said divergent tape and liner paths being defined by a lower inside surface of a front wall of said casing, a concavely curved inside surface of a bottom wall portion of said casing, and the convexly curved surface of said post, said resilient depressible wall portion comprising a depressible flap portion of said front wall operable to selectively press a section of tape and liner passing along said front wall against said post, the marginal edge portions of said liner extending laterally slightly beyond the marginal edge portions of said tape to prevent the adhesive backing of said tape from fouling said casing.

* * * * *